United States Patent [19]
Haugland et al.

[11] Patent Number: 5,635,608
[45] Date of Patent: Jun. 3, 1997

[54] α-CARBOXY CAGED COMPOUNDS

[75] Inventors: Richard P. Haugland, Eugene; Kyle R. Gee, Springfield, both of Oreg.

[73] Assignee: Molecular Probes, Inc., Eugene, Oreg.

[21] Appl. No.: 336,284

[22] Filed: Nov. 8, 1994

[51] Int. Cl.$^6$ .............................. C07H 1/00; C13K 13/00; C07F 9/02; C07F 9/28; C07F 9/22; C07C 229/00; C07C 59/48

[52] U.S. Cl. ............... 536/1.11; 536/123.1; 536/123.13; 548/413; 548/526; 549/221; 549/430; 554/103; 554/104; 560/16; 560/20; 560/22; 560/24; 560/43; 560/45; 560/55; 560/84; 562/8; 562/9; 562/24; 562/426; 562/434; 562/470; 562/471

[58] Field of Search ..................... 560/173, 16, 20, 560/22, 24, 43, 45, 55, 84; 548/413, 526; 554/103, 104; 549/221, 430; 562/8, 9, 24, 426, 434, 470, 471; 536/1.11, 123.1, 123.13

[56] References Cited

U.S. PATENT DOCUMENTS

| | | | |
|---|---|---|---|
| 4,945,171 | 7/1990 | Haugland et al. | 549/224 |
| 5,227,487 | 7/1993 | Haugland et al. | 546/15 |

OTHER PUBLICATIONS

Krebs, et al., Chem. Ber. (89), 875–83 1956.
Wieboldt, et al. Proc. Natl. Acad. Sci. 91(19) pp. 8752–8756 Sep. 13, 1994.
Walker, et al. J. Biol Chem. 267(4), 2459 1992.
Corrie, J. Chem Soc, Perkin Trans. 1, 2161 (1993).
Walker, et al., Biochem, 32, 1338 (1993).
Wieboldt, et al., Biochem, 33, 1526 (1994).
Corrie, et al., J. Physiol, (London) 465, 1 (1993).
Ramesh, et al., J. Org. Chem. 58, 4599 (1993).
Milburn, et al., Biochem 28, 49 (1989).
Walker, et al., J. Am. Chem. Soc. 110, 7170 (1988).
Wilcox, et al., J. Org. Chem. 55, 1585 (1990).
Wieboldt, et al., PNAS/USA 91(19), 8752 (1994).
Cummings, et al., Tet. Lett. 29, 65 (1988).

*Primary Examiner*—Joseph Conrad
*Attorney, Agent, or Firm*—Allegra J. Helfenstein; Anton E. Skaugset

[57] ABSTRACT

The invention relates to caged compounds for the study of biological processes, where the caged compound has a photoremoveable α-carboxy-substituted o-nitrobenzyl group. Covalent attachment of the substituted o-nitrobenzyl to a parent compound yields a caged compound with biological and/or physical properties that are significantly altered from the original properties of the parent compound. Illumination of the caged compounds to cleave the photoremoveable group yields the parent compound with its original properties restored.

23 Claims, 3 Drawing Sheets

α-CARBOXY CAGED COMPOUNDS

FIELD OF THE INVENTION

The invention relates to organic compounds that are caged with a photoremoveable group that changes the fluorescence or biological properties of the compound. In particular, the organic compounds are carboxylic, carbonic, carbamic, phosphonic or thiophosphonic acid derivatives, or thiols or alcohols, that contain a photoremoveable α-carboxy-substituted o-nitrobenzyl group and undergo an extremely rapid rate of photolysis to yield a biologically active or fluorescent compound.

BACKGROUND

Covalent attachment of photoremoveable group to a parent compound (i.e. "caging") to alter its physical or biological properties has been exploited extensively for following components of dynamic systems. The term "cage" refers to a photolytically sensitive substituent that is designed to interfere with the reactivity or other physical properties of the free probe. Photolysis (typically by illumination in the UV (250–400 nm) region of the spectrum) cleaves off the caging group, restoring the normal properties of the parent compound. In this way it is possible to release the parent compound into the system of interest with much better temporal and spatial resolution than is possible by simple diffusion.

In the use of caged compounds for the study of processes that change rapidly, such as biological processes that occur on the time scale of a millisecond or faster, it is critical that photolysis also occur very rapidly and with relatively high quantum yield. Also of critical importance is that the caged compound is stable and still soluble in the system of interest, and that caging reduces some property of the parent compound to the desired level. The o-nitrobenzyl group and its substituted variants have been widely used to prepare caged versions of biologically active substances by attachment at a variety of terminal substituents, including e.g. aliphatic hydroxyls (J. Chem. Soc. Perkin Trans. 1,2161 (1993)); phenolic hydroxyls (Biochem. 32, 1338 (1993)); amines (caged as o-nitrobenzylamines (Biochem. 33, 1526 (1994)) and also as o-nitrobenzylcarbamates (J. Physiol. (London) 465, 1 (1993)); amides (caged on the nitrogen (J. Org. Chem. 58, 4599 (1993)), carbamates (caged on the nitrogen (Biochem. 28, 49 (1989)), phosphates (J. Am. Chem. Soc. 110, 7170 (1988)); and carboxylates (caged as o-nitrobenzyl esters) (J. Org. Chem. 55, 1585 (1990)). Unfortunately, the photolysis properties have varied widely with both the caged compound and the substitution pattern on the o-nitrobenzyl caging group, i.e. photolysis rates from <1 s$^{-1}$ up to 10$^5$ s$^{-1}$, and quantum yields ranging from <0.01 up to 0.8, and efforts at preparing caged materials with the characteristics desired for use in biological systems have met with limited success.

For example, many biologically active materials, e.g. neurotransmitters, peptides, proteins, hormones, second messengers, contain carboxylic acid moeities. Carboxylates caged as their o-nitrobenzyl esters, however, photolyze only with low quantum yield (<0.01) and at a very low rate (ca. 1 s$^{-1}$) (11). Mother problem has been that caging of carboxylates as their o-nitrobenzyl esters significantly dishes their solubility in aqueous systems. A recently reported caging group for the carboxylate function of glycine (2-methoxy-5-nitrophenoxy ester) is photolyzed in the microsecond time region with a 0.2 quantum yield but is hydrolyrically unstable and thus not useful for biological applications (12). Some functionalities have been caged with the α-carboxy-o-nitrobenzyl substituent, i.e. phenols (Biochem. 32, 1338 (1993)), amines (Biochem. 33, 1526 (1994)), amides (J. Org. Chem. 58, 4599 (1993)), and carbamates (Biochem. 28, 49 (1989)), with generally favorable results; yet a comparison of caged compounds that were prepared by attaching a substituted or unsubstituted o-nitrobenzyl group (including N-α-carboxy-o-nitrobenzyl) at the terminal amine of the neurotransmitter glutamate showed mixed results (Table 1; Compounds A, B, C). Utilizing this comparison, the γ-(α-methyl-o-nitrobenzyl) ester of glutamate (D) was prepared; however, its photolysis rate (9 s$^{-1}$) and quantum yield (very low) were unacceptable (PNAS/USA 91 (19), 8752 (1994)). In contrast to the previous results, however, attachment of an α-carboxyl substituent to the γ-(o-nitrobenzyl) ester of glutamate unexpectedly provided a water-stable compound (3) with dramatically improved photolysis rate and quantum yield, several orders of magnitude over previously prepared versions of o-nitrobenzyl-caged carboxylates (J. Org. Chem. 55, 1585 (1990)). This caging group can be used to prepare caged versions of a number of biologically useful acid derivatives. Furthermore, attachment of this α-carboxy-o-nitrobenzyl ester to carboxylates maintains the aqueous solubility that has normally been lost in the past by converting carboxylates into their o-nitrobenzyl esters.

TABLE 1

Relative rates of photolysis for related caged compounds.

Compound A: R = H
Compound B: R = CO$_2$H
Compound R = CH$_3$

Compound D: R = CH$_3$
Compound 3: R = CO$_2$H

| Compound | k (s$^{-1}$) at 308 nm | Φ |
|---|---|---|
| A | 210 | <0.01 |
| B | 385 | 0.04 |
| C | 2,240 | 0.06 |
| D | 9 | <0.01 |
| 3 | 24,800 | 0.16 |

DESCRIPTION OF DRAWINGS

FIG. 2: The photolysis of a caged probe in situ, as described in Example 15. The increase in whole-cell current upon illumination (time=0) indicates that the probe (glutamic acid) is inert when caged, but the active form is rapidly released upon illumination.

SUMMARY OF THE INVENTION AND DESCRIPTION OF PREFERRED EMBODIMENTS

The caged compounds of the invention are produced by covalent attachment of a photoremoveable α-carboxy-substituted o-nitrobenzyl group (CAGE) as an ether of an aliphatic alcohol ($R^5$—OH), a thioether of a thiol ($R^5$—SH), or as an ester of a carboxylic acid ($R^5$—(C=O)—OH), a carbonic acid ($R^5$—O—(C=O)—OH), a chlorocarbonic acid (HO—(C=O)—Cl), a carbamic acid ($R^5$—NH—(C=O)—OH or $R^5R^6$—N—(C=O)—OH)), a phosphoric acid ((HO—P(=O)—(OH)$_2$, $R^5$—O—P(=O)—(OH)$_2$ or ($R^5$—O)($R^6$—O)—P(=O)—OH)), or a thiophosphoric acid ((HO)$_2$—P(=O)—SH), $R^5$—S—P(=O)—(OH)$_2$, $R^5$—O—P(=S)—(OH)$_2$, $R^5$—O—(P=O)—(OH)(SH), ($R^5$—O)($R^6$—O)—P(=S)—OH or ($R^5$—O)($R^6$—O)—P(=O)—SH).

The CAGE component of the photolabile precursor has the formula:

The cage substituents $R^1$ and $R^2$, which may be the same or different, are H, —(C=O)—Cl, —$CO_2R^7$, —$OR^8$ or —O—$(CH_2)_n$—$CO_2R^7$, where $R^7$ is H, a linear or branched alkyl ester containing 1–6 carbons, an acetoxymethyl ester (—$CH_2$—O—(C=O)—$CH_3$), or a succinimidyl ester, or a carboxylate salt, and $R^8$ is a linear or branched alkyl having 1–18 carbons and n=1–17. Alternatively, $R^1$ and $R^2$ taken in combination are —O—$CH_2$—O—. Preferably $R^1$ and $R^2$ are both hydrogen.

A carboxylate salt means a cationic counterion of a carboxylate anion used to improve the solubility of the compound in selected solvents. Examples include $K^+$, $Na^+$, $Cs^+$, $Li^+$, $Ca^{2+}$, $Mg^{2+}$, or $NR_4^+$ salts, where R=H, $C_1$-$C_4$ alkyl, or $C_2$-$C_4$ alkanol, or combinations thereof.

The careful selection of substituent $R^7$ can be used to modify the solubility properties of the caged product, such as for the purpose of enhancing its uptake by biological cells, or $R^7$ substituents may permit the covalent attachment of the caged molecule to another organic molecule, such as for the purpose of targeting the caged molecule to a specific location or limiting diffusion of the caged molecule, or selected $R^7$ substituents may temporarily block the reactivity of the carboxylic acid while carrying out desired synthetic modifications on other parts of the molecule.

The cage substituent $R^3$ is hydrogen or nitro. Preferably $R^3$ is hydrogen.

The carboxyl substituent $R^4$ is H, chloro, a linear or branched alkyl ester containing 1–6 carbons, an acetoxymethyl ester (—$CH_2$—O—(C=O)—$CH_3$) or a succinimidyl ester, or a carboxylate salt. Preferably $R^4$ is hydrogen or an acetoxymethyl ester.

Typically, substituents $R^1$, $R^2$, $R^3$ and $R^4$ are hydrogen.

Where the initial photoproduct formed by removal of CAGE is a carbamic acid or a carbonic acid this product is unstable and decomposes essentially spontaneously to an aliphatic alcohol ($R^5$—OH) or an amine ($R^5NH_2$ or $R^5R^6$—NH). The caged esters of carboxylic acids, phosphoric acids and thiophosphoric acids are chemically stable and do not undergo subsequent spontaneous decomposition reactions. Where CAGE is directly attached through an ether of thio ether bond the final photoproducts are alcohols (including aromatic alcohols) ($R^5$—OH) or thiols (including thio analogs of aromatic alcohols, ($R^5$—SH) respectively.

The photolytic removal of CAGE depends only on the presence of the o-nitrobenzyl moiety and a single benzylic hydrogen atom and its covalent attachment to $R^5$ and, where present $R^6$, through one of the chemical bonding structures indicated above and depends to only a limited extent on the chemical nature of either $R^5$ or $R^6$. The component $R^5$, and where present $R^6$, forms the remainder of the residue to which CAGE is attached in the linkage specified above to yield a caged compound with altered physical or biological properties. Photolysis of the caged compound yields a photoproduct containing the component $R^5$, and where present $R^6$, that in combination with a terminal moiety of the photoproduct is a thiol, a carboxylic acid, a carbonic acid, a chlorocarbonic acid, a carbamic acid, a phosphoric acid, or a thiophosphoric acid, according to the list of photoproducts described below. The component $R^5$, and where present $R^6$, range in size from a single atom such as H or halide (e.g. Cl) to a polymeric residue such a dextran or oligonucleotide, and are optionally the same or different or $R^5$ and $R^6$ combine to form a heterocyclic ring structure, such as where the caged compound is a secondary amine or a phosphate that it is a phosphodiester of a cyclic diol, or $R^5$ and $R^6$ combine with different functionalities of the same molecule, such as different sugars on a nucleic acid. Preferably, photolysis yields the photoproducts $R^5$—OH, $R^5$—SH, $R^5$—(C=O)—OH, $R^5$—$NH_2$, $R^5R^6$—NH, (HO—P(=O)—(OH)$_2$, $R^5$—O—P(=O)—(OH)$_2$, (HO)$_2$—P(=O)—SH), $R^5$—O—P(=O)—(OH)(SH), $R^5$—S—P(=O)(OH)$_2$, ($R^5$—O)($R^6$—O)—P(=O)—OH, ($R^5$—O)—P(=O)—SH) that include the component $R^5$ and, where present $R^6$, to form either a biologically active molecule or a fluorescent dye.

A biologically active molecule, as used herein, is a natural molecule that is found naturally in living systems such as animals or plants, or is a synthetic molecule that would elicit a biological response in a living organism. This response may be essentially immediate, such as an effect on the conformation, bonding, binding, electrical, or osmotic properties of a cell, tissue, organ or organism. Alternatively, the response may be a delayed response that requires metabolism of the initial photoproduct or formation of an antibody to the product. A caged biologically active molecule, as used herein, is any molecule containing at least one CAGE, whether or not it is brought into contact with a biological sample.

Preferred biologically active molecules are carboxylic acids, dicarboxylic acids and polycarboxylic acids; amino acids, peptides, proteins; carbohydrates; nucleosides, nucleotides, oligonucleotides and nucleic acids; or drugs, hormones and haptens.

Carboxylic acids are linear or branched, saturated or unsaturated, substituted or unsubstituted, molecules containing 1 to 32 carbons. They include lower and fatty acids such as acetic acid, oleic acid, or arachidonic acid; substituted fatty acids such as prostaglandins, domoic acid; partially cyclic fatty acids such as cholic acids; and polycarboxylic acids such as citric acid.

Selected amino acids are caged through either the carboxylic acid as an ester, through the α-nitrogen atom as a carbamate, through a non-α-nitrogen (as in lysine or γ-aminobutyric acid) or as an ether or carbonate of a side-chain hydroxyl (as in serine, threonine or tyrosine) or as a thio ether (as in cysteine), or as an ester of a phosphorylated amino acid such as phosphotyrosine, phosphoserine or phosphothreonine. The amino acid may be natural or synthetic, optically active or non-optically active and optionally contains additional groups such as are required for the synthesis of peptides containing CAGE. Furthermore, the amino acid is optionally incorporated into a natural or synthetic peptide or at one or more sites in a protein. Alternatively, the caged amino acid is incorporated as the first or subsequent residue in the synthesis of a peptide, such as is done using an automated peptide synthesizer.

Selected carbohydrates include monosaccharides, disaccharides and polysaccharides that may be branched or unbranched, crosslinked or not crosslinked, water soluble or not water soluble. The chemistry of conjugation is as a ether or carbonate of an aliphatic hydroxyl group, as a carbamate of an amino group, or as an ester of a carboxylic acid or of a phosphate or thiophosphate group. The carbohydrate can be further conjugated to a protein, lipid, solid phase, dye, drug, hapten, nucleoside, nucleotide or oligonucleotide. The carbohydrate is optionally a simple carbohydrate, such as glucose or glucose-1-phosphate, or a complex carbohydrate such as inositol-1,4,5-triphosphate, 4-methylumbelliferyl β-D-glucuronide.

Selected nucleosides, nucleotides, oligonucleotides and nucleic acids are optionally natural or synthetic and optionally contain natural or unnatural sugars and natural or unnatural linkages between sugars. Selected nucleosides, nucleotides or nucleic acids optionally contain additional substitutions on the base, sugar or phosphate portions, such as those required to temporarily protect the molecule during the synthetic coupling steps required to prepare synthetic oligonucleotides. Substitution of CAGE is as an ether or carbonate ester of the carbohydrate portion or of a hydroxyl function attached directly or indirectly to the base. Alternatively, CAGE is attached as a carbamate derivative at a nitrogen atom of base, or CAGE is attached as an ester of phosphate or thiophosphate. When CAGE is attached as an ester of phosphate or thiophosphate, the biologically active molecule is a monophosphate such as adenosine-3'-monophosphate, a diphosphate such as 2'-deoxyadenosine-5-diphosphate, a triphosphate such as guanosine-5'-diphosphothiophosphate (GTP-γ-S) or a polyphosphate such as a caged 5'-phosphate ester of the oligonucleotide ApTpGpC. The biologically active phosphate may be a phosphate mono ester (in which case $R^4$ in the biologically active molecule) or a phosphodiester (including cyclic phosphate esters such as adenosine-3',5-cyclicmonophosphate (cAMP), adenosine-3',5-cyclicmonophoshorothioate (cAMP-S), and cyclic adenosinediphosphoribose (cADPribose).

Selected drugs, hormones and haptens are preferably organic molecules with molecular weights less than 10,000 Daltons, more preferably less than 1000 Daltons. A drug, as used herein, is a natural or synthetic molecule that is a ligand for some biological receptor. The receptor may be a protein such as an antibody, enzyme or membrane-bound receptor. The receptor may be part of a cell, incorporated into another matrix such as a liposome or in a cell free medium. In the case of this type of caged molecule, the site of attachment of CAGE to the drug, hormone or hapten is chosen so as to interfere with the normal biological response to the drug, hormone or hapten. This can be determined by synthesis of the caged drug through one of the permitted functional groups usually using methods well known to one skilled in the art, and comparing the response to the caged drug, hormone or hapten versus the response to the non-caged form of the drug, hormone or hapten. The response being measured may be any of those listed above or any other test than allows the comparison of the caged and uncaged forms of the drug, hormone or hapten. Usually it is only necessary to incorporate a single CAGE in the molecule to block it biological activity. In some cases such as proteins, polysaccharides or oligonucleotides it may be necessary to incorporate multiple CAGE moieties.

Preferred drugs, hormones and haptens are those with a high affinity for some known or unknown biological receptor. By high affinity is meant an apparent first order dissociation constant of less than $10^{-5}$ M, preferably less than $10^{-6}$ M and most preferably less than $10^{-8}$ M. A wide variety of natural and synthetic drugs, including drugs of abuse, that bind to dopaminergic, serotonergic, adrenergic, cholinergic, benzodiazepine, andothelin, histamine, acetylcholine, opioid, purinergic, and sigma receptors are known. Methods of the design, synthesis, and testing for biological activity of existing and new drugs are widely known and extensively practiced, particularly in the drug industry.

In one aspect of the invention the drugs, hormones and haptens are natural ligands for known biological receptors. These include excitatory amino acids such as glycine, γ-aminobutyric acid, N-methyl-D-aspartic acid and glutamic acid; carboxylic acids such as arachidonic acid and domoic acid, alcohols such as phorbol esters and steroidal hormones, peptides such as insulin and α-bungarotoxin, haptens such as biotin and digoxigenin.

Most commonly, when the site on the drug, hormone or hapten to be caged is an amine it is a primary amine and the photoproduct is $R^5$—$NH_2$. Less commonly it is a secondary amine, in which case the structure of $R^5$ is determined by the overall structure of the drug, hormone or hapten. Often this is lower alkyl. It is also not uncommon for secondary amines to be cyclic compounds in which $R^5$ and $R^6$ combine to form a single heterocyclic ring that usually contains 5 to 7 ring atoms and that is optionally fused one or more times to additional rings that are aromatic, heteroaromatic, alicyclic or heterocyclic.

Haptens are molecules for which there exist or can be prepared antibodies or other specific binding proteins such as a lectin or avidin. In this case caging is intended to prevent recognition of the caged molecule by its specific binding protein, commonly by steric interference with ligand binding.

The other preferred photoproducts are fluorescent dyes. In this embodiment the photoproduct is a fluorescent phenol, amine, carboxylic acid, phosphate or thiophosphate. Most preferred are derivatives in which incorporation of the caging group results in the caged product being essentially nonfluorescent or having absorption spectra that are shifted toward the ultraviolet relative to the uncaged dye. The caged dye may have a single CAGE moiety, may have two CAGE moieties or less often may have more than two CAGE moieties. Incorporation of the CAGE beating a free carboxylic acid or it salt can be used to improve the dye's water solubility and, when $R^7$ is a chemically reactive group such as chloro or a succinimidyl ester, this substitution can be used to conjugates the caged dye to another organic molecule.

In one embodiment, the photoproduct is a phenol or polyphenolic moiety. Typically this is a dye that has one to five fused or non-fused rings. Many of these phenolic dyes are commonly recognized fluorophores including, among others, naphthols, hydroxycoumarins, hydroxyanthracenes, hydroxypyrenes, fluoresceins, benzofluoresceins, naphthofluoresceins, hydroxyoxazines (such as resorufins) and acridinones.

In a second embodiment, the photoproduct is a primary or a secondary amine. In the latter case $R^5$ is lower alkyl with 1 to 6 carbons or $R^5$ in combination with an adjacent ortho position on the fluorophore forms a saturated 5- or 6-membered ring. Common amine-containing fluorescent dyes include, among others, anthranilic acids, aminonaphthalenes, aminocoumarins, aminoanthracenes, aminopyrenes, rhodamines, aminooxazines and aminoacridinones.

In a third embodiment, the photoproduct contains both an amine and a hydroxy function and one or both of these functions are caged. An example are the rhodol fluorophores or the seminaphthorhodafluor dyes described in U.S. Pat. No. 5,227,487 to Haugland et al. (1993) and U.S. Pat. No. 4,945,171 to Haugland et al. (1990).

Whereas covalent attachment of the substituted o-nitrobenzyl to a parent compound yields a caged compound with biological and/or physical properties that are significantly altered from the original properties of the parent compound; conversely, illumination of the caged compounds to cleave the photoremoveable group yields the parent compound with its original properties restored.

The compounds of the present invention are photolysed to cleave CAGE and release the biologically active probe. This photolytic illumination will typically have a wavelength of less than 400 nm, preferably less than 360 nm. Although the photolytic illumination will typically have a wavelength greater than 200 nm, in order to prevent damage to biological systems (when present) the illumination will preferably have a wavelength greater than 300 nm. The photolysis illumination of compounds of the present invention is completely analogous to photolysis procedures known in the art for other caged probes, and is well known to one of ordinary skill. Illumination of the caged compound within the absorption bands of CAGE is required, typically using a light source capable of radiation at less than about 400 nm. Typical light sources include mercury arc lamps, flash lamps and lasers such as nitrogen lasers. The photolytic illumination is typically generated using an ultra-violet laser. Photolysis of a solution of a compound of the present invention will typically produce a mixture of caged and free probes.

The caged compound is optionally photolysed in a biological system to yield a biologically active or fluorescent photoproduct in situ to allow rapid but controlled release of the biologically active material to to initiate or block intracellular function and analyze the biological system, e.g. to study the dynamics of the biological system, intercellular communication, cell or tissue development, intracellular structure, transport across membranes etc. Alternatively, the caged compound is photolysed in a solution to release a chemically reactive photoproduct that reacts with other natural or synthetic intermediates to complete a chemical synthesis. The utilization of photolysis to release selected photoproducts at a desired time and space is well known in the art. The object of this invention is to provide improved materials for a wide variety of applications.

Synthesis

Some generally useful key intermediates allow the synthesis of a wide variety of caged products to be prepared by well-recognized routes. In most cases, the initially caged derivative has a protecting group on the carboxylic acid, which is removed in a subsequent reaction to form the carboxy-caged probe. Usually this group is a tert-butyl group, which is removed by treatment with an acidic reagent such as trifluoroacetic acid.

The following routes are preferred routes for synthesis of the subject caged probes: Carboxylic acids (as esters): reaction of the free carboxylic acid with the diazoalkyl intermediate 25 (Example 9), or reaction of a salt of the carboxylic acid with the benzylic bromide 1 (Examples 1–5), or direct esterification of the benzylic alcohol 18 with an acid halide, or anhydride. Phosphoric acid or thiophosphoric acid (O-caged) (as esters): reaction of the free phosphoric acid or thiophosphoric acid with a diazoalkane 25 (Example 10), or reaction of the benzylic alcohol 18 with phosphorous oxychloride/pyridine followed by addition of $R^5$—OH (Example 11).

Thiophosphate esters (S-caged): displacement of the benzylic bromide 1 by the thiophosphate (Example 13).

Amines (as carbamates): Reaction of the chloroformate 14 with $R^5NH_2$ or $R^5R^6NH$ (Example 6) or reaction of an isocyanate ($R^5$—N=C=O) with the benzylic alcohol 18.

Alcohols (as carbonates): Reaction of the chloroformate 19 with an alcohol $R^5$—OH (Example 7). Alcohols (as ethers): Reaction of the alkoxide with the benzylic bromide 1.

Thiols (as thioethers): Reaction of the thiol or its salt with the benzylic bromide 1 (Example 12).

Of particular importance as synthetic intermediates are chloroformate such as 14 and 19, which can be used to cage most any alcohol (including phenols) or primary or secondary amine (including aromatic amines), and diazoalkanes such as 25, which can react with both carboxylic acids and phosphoric acids.

Modifications at $R^1$, $R^2$ and/or $R^3$ can be used to shift the activation spectrum for photolysis to longer wavelengths or to provide points of attachment for other organic groups or, in the case of $R^3$ being nitro, to further accelerate the photolysis rate (TET. LETT. 29, 65 (1988)).

Modification of the carboxylic acid of the caged probes at $R^4$ is usually accomplished subsequent to caging of the biologically active molecule or the dye. Incorporation of acetoxymethyl esters is usually done by reaction of bromomethyl acetate with the carboxylic acid salt (Example 8). Activation of the carboxylic acid as an acid chloride, succinimidyl ester or a wide variety of other "activated esters" is commonly done on probes that contain no nucleophiles and that are soluble in organic solvents such as dimethylformamide. Acid chlorides are prepared using thionyl chloride, phosphorous oxychloride or other chlorinating agents. Amine-reactive succinimidyl esters are prepared by one of several methods known in the art. Once formed, the activated esters can be coupled to nucleophiles found on peptides, proteins, oligonucleotides, nucleic acids, polymers (including natural and synthetic polymers), lipids and phospholipids, drugs, amine-modified glass, and other organic and inorganic molecules.

The examples below are given so as to illustrate the practice of this invention. They are not intended to limit or define the entire scope of this invention.

EXAMPLES

Example 1. L-Glutamic Acid, γ-(α-carboxy-o-nitrobenzyl) ester (3):

A solution of N-t-BOC-L-glutamic acid, α-t-butyl ester (240 mg, 0.79 mmol, Sigma), t-butyl(2-bromo-2-o-nitrophenyl)acetate (1) (250 mg, 0.79 mmol) and diazabicycloundecane (DBU, 125 mg, 0.82 mmol) in benzene (10 mL) is heated at reflux for 5 hours. After cooling, the reaction mixture is partitioned between ethyl acetate (20 mL) and water (20 mL). The organic layer is dried using anhydrous sodium sulfate and concentrated to give a pale brown oil, which is purified using flash chromatography (EtOAc/CHCl$_3$, 0% to 5%) to give the protected intermediate 2 as a clear colorless oil (0.34 g, 80%): R$_f$0.35 (5% EtOAc/CHCl$_3$); $^1$H NMR (CDCl$_3$) 8.01 (d, J=8.1 Hz, 1 H, C3—H) 7.67 (m, 2 H, C4,5—H), 7.52 (m, 1 H, C6—H), 6.76 (d, J=5.15 Hz, 1 H, ArC$\underline{H}$), 5.11 (m, 1 H, CO$_2$C$\underline{H}$N), 4.2 (br s, 1 H, N$\underline{H}$), 2.7–1.9 (m, 4 H, CO$_2$C$\underline{H}_2$C$\underline{H}_2$), 1.4 (m, 27 H, C(C$\underline{H}_3$)$_3$).

To 2 at room temperature under argon is added 30% trifluoroacetic acid (TFA) in CHCl$_3$ (10 mL), and the resulting solution is allowed to stand for three hours. The volatiles are removed under vacum, and toluene is added followed by re-evaporation under vacuum (2×15 mL). The resulting pale brown oil was purified by chromatography on SEPHADEX LH-20 resin, using water as eluant, giving 135 mg (50%) of 3 as a fluffy colorless powder after lyophilization: m.p. 122°–125° C. (dec.); $^1$H NMR (D$_2$O) 8.13 (d,J= 7.8 Hz, 1 H, C3-$\underline{H}$), 7.80 (m, 1 H, C5-$\underline{H}$), 7.7 (m, 2 H, C4,6-$\underline{H}$), 6.68 (s, 1 H, ArC$\underline{H}$), 4.08 (t, J=6.4 Hz, 1 H, CO$_2$C$\underline{H}$N), 2.7 (m, 2 H, CO$_2$C$\underline{H}_2$CH$_2$), 2.25 (m, 2 H, CO$_2$CH$_2$C$\underline{H}_2$). Anal. Calcd for C$_{15}$H$_{15}$N$_2$O$_{10}$F$_3$: C, 40.92; H, 3.43; N, 6.36. Found: C, 42.27; H, 3.81; N, 6.74.

Example 2. L-Glutamic Acid, α-(α-carboxy-o-nitrobenzyl)ester (5):

A solution of N-t-BOC-L-glutamic acid, γ-t-butyl ester (221 mg, 0.73 mmol), bromo derivative 1 (0.21 g, 0.66 mmol), and diazabicycloundecane (DBU, 116 mg, 0.76 mmol) in benzene (10 mL) is refluxed overnight. After cooling, water (30 mL) is added and the layers are separated. The aqueous layer is extracted with ethyl acetate (2×15 mL). The combined organic portions are washed with brine (1×), dried over sodium sulfate, and concentrated in vacuo to give 0.37 g of a brown oil, which is purified by flash chromatography (EtOAc/chloroform 0% to 5%) to give 0.30 g (84%) of intermediate 4 as a clear colorless oil that is a 1:1 mixture of diastereomers: $^1$H NMR (CDCl$_3$) 8.03 (2d, J=8.23 Hz, 1 H, C3-$\underline{H}$), 7.67 (m, 2 H, C4,5-H), 7.51 (m, 1 H, C6-H), 6.84, 6.78 (2s, 1 H, ArC$\underline{H}$CO$_2$), 5.11 (m, 1 H, N$\underline{H}$), 4.46 (m, 1 H, CO$_2$C$\underline{H}$N), 2.5–1.9 (m, 4 H, CO2C$\underline{H}_2$C$\underline{H}_2$), 1.4 (m, 27 H, C(C$\underline{H}_3$)$_3$).

A solution of 4 (0.29 g, 0.54 mmol) in 40% TFA/chloroform (10 mL) is allowed to stand at room temperature for 24 hours, then concentrated in vacuo. Benzene was added to the residue and removed under vacuum (2×10 mL, leaving a pale brown oil. This oil is dissolved in water (20 mL) and lyophilized, giving 223 mg (94%) of 5 as a pale brown crystalline solid that is a mixture of diastereomers: $^1$H NMR (D$_2$O) 8.17 (d, J=8.1 Hz, 1 H, C3-$\underline{H}$), 7.84 (t, J=7.6 Hz, 1 H, C5-$\underline{H}$), 7.70 (m, 2 H, C4,6-$\underline{H}$), 6.8 (two s, 1 H, ArC$\underline{H}$CO$_2$), 4.4 (two t, J=6.6 Hz, 1 H, CO$_2$C$\underline{H}$N), 2.76 (dt, J=8.0, 1.9 Hz, 1 H, CO$_2$C$\underline{H}_2$CH$_2$), 2.6–2.2 (m, 3 H, CO$_2$CH$_2$C$\underline{H}_2$). An analytical sample is prepared by chromatography using SEPHADEX LH-20 resin, giving the title compound as a fluffy colorless powder; m.p. 130–134° C. (dec.). Anal. calcd (C$_{15}$H$_{15}$N$_2$O$_{10}$F$_3$) C, 40.92; H, 3.43; N, 6.36. Found: C, 41.45; H, 3.82; N, 6.62.

Example 3. o-Nitro-α-carboxybenzyl 4-amino-butyrate (6):

A solution of 1 (0.26 g, 0.82 mmol), N-t-BOC-γ-aminobutyric acid (166 mg, 0.82 mmol) and DBU (0.13 mL, 0.87 mmol) in benzene (10 mL) is heated at reflux overnight. The DBU hydrobromide is filtered, and the filtrate concentrated to a pale brown oil, which is purified by flash chromatography (5% ethyl acetate/chloroform) to give 0.36 g (100%) of α-t-butylcarboxyl-2-nitrobenzyl N-t-BOC-γ-aminobutyrate as a clear, pale brown oil: $^1$H NMR (CDCl$_3$) 8.00 (d,J=7.6 Hz, 1 H), 7.64 (m, 2 H), 7.53 (m, 1 H), 6.74 (s, 1 H), 4.7 (br s, 1 H), 3.20 (q, J=6.3 Hz, 2 H), 2.52 (m, 2 h), 1.90 (m,J=6.9 Hz, 2 H), 1.43 (s, 9 H), 1.40 (s, 9 H).

Neat α-t-butylcarboxyl-2-nitrobenzyl N-t-BOC-γ-aminobutyrate (0.30 g, 0.68 mmol) is cooled in an ice bath under argon, and treated with trifluoroacetic acid (2.2 mL, 29 mmol). The resulting solution is incubated overnight at room temperature. The volatiles are removed in vacuo to give a pale brown oil. This oil was purified by chromatography on SEPHADEX LH-20 resin, using water as eluant. The combined product fractions are lyophilized to give 210 mg (77%) of the trifluoroacetate salt of 6 as a compact colorless powder: m.p. 139–142° C. dec.; $^1$H NMR (D$_2$O) 8.13 (d, J=8.1 Hz, 1 H), 7.81 (t, J=7.4 Hz, 1 H), 7.70 (m, 2 H), 6.69 (s, 1 H), 3.07 (t,J=6.4 Hz, 2 H), 2.63 (m, 2 H), 2.01 (t, J=7.0 Hz, 2 H). Anal. calcd for C$_{14}$H$_{15}$N$_2$O$_8$F$_3$: C, 42.43; H, 42.45; N, 7.07. Found: C, 42.45; H, 3.97; N, 6.92.

Example 4. (S)-Bis-α,β-(O-(α-(t-butoxycarbonyl)-2-nitrobenzyl))-N-(t-butoxycarbonyl)-N-methylaspartate (9):

N-Methyl-D-aspartic acid (NMDA, RBI) (1.00 g, 6.80 mmol) is suspended in a solution of water/dioxane (1:1, 10 mL) at room temperature. Sodium bicarbonate (1.77 g, 21.1 mmol) is added, followed by a solution of t-butylpyrocarbonate (1.75 g, 8.00 mmol) in 4 mL dioxane. The resulting colorless mixture is stirred for 48 hours, then treated with another portion of pyrocarbonate (1.00 g, 4.58 mmol) in 2 mL dioxane and sodium bicarbonate (0.47 g, 5.6 mmol). After another 24 hours, the reaction mixture is diluted with water (10 mL) and extracted with EtOAc (3×10 mL). The pH (8.5) of the aqueous mixture is adjusted to 3.0 with 5% HCl, followed by extraction with EtOAc (3×10 mL). The extract is dried over sodium sulfate and concentrated to give 1.30 g (77%) of N-t-BOC NMDA as a clear colorless viscous oil: R$_f$(MeCN/H$_2$O/AcOH 8:1:1) 0.73; $^1$H NMR (CDCl$_3$) 4.76, 4.55 (two br s, 1 H, NC$\underline{H}$), 3.15 (dd, J=17.0, 7.0 Hz, 1 H, C$\underline{H}_2$), 2.94 (br d, J=19.9 Hz, 3 H, N Me), 2.83 (td,J=17.0, 7.3 Hz, 1 H, C$\underline{H}_2$), 1.45 (s, 9 H, C(C$\underline{H}_3$)).

To a colorless solution of N-t-BOC NMDA (0.42 g, 1.7 mmol) and 1 (1.04 g, 3.40 mmol) in a solution of benzene/THF (20 mL/5 mL) at room temperature is added DBU (0.52 mL, 3.50 mmol). The resulting deep blue mixture is heated at reflux for six hours, then cooled and filtered using a WHATMAN #1 filter paper). The filtrate was concentrated, and the residue purified by flash chromatography (EtOAc/CHCl$_3$, 0 to 5%) to give tetraester 0.57 g (50%) of 7 as a clear, pale brown mobile oil that is a mixture of diastereomers: R$_f$(5% EtOAc/CHCl$_3$) 0.42; $^1$H NMR (CDCl$_3$) 8.0 (m, 2 H, Ar-3-$\underline{H}$), 7.7-7.4 (m, 6 H, Ar-4,5,6-$\underline{H}$), 6.76 (m, 2 H, ArC$\underline{H}$), 3.64 (d,J=4.6 Ha, 1 H, NC$\underline{H}$), 3.5-3.0 (m, 2 H, C$\underline{H}_2$), 3.46 (m, 3 H, NMe), 1.5-1.3 (m, 27 H, C(C$\underline{H}_3$)).

To a solution of the tetraester 7 (0.54 g, 0.75 mmol) in dioxane (5 mL) at room temperature is added a solution of NaOH (30 mg, 0.75 mmol) in water (1 mL). The resulting pale brown mixture is stirred for 48 hours. The volatiles are removed in vacuo, and the residue is dissolved in 25 mL saturated sodium bicarbonate solution. The resulting mixture is extracted with EtOAc (2×15 mL), and the aqueous layer acidified to 2.7 by addition of 5% HCl. The resulting mixture is extracted with EtOAc (3×15 mL). The combined extracts are treated with activated charcoal and filtered using diatomaceous earth, and concentrated to yield a pale brown oil. This oil was purified by flash chromatography to give 0.17 g (47%) of the bis-ester 8 as a clear pale brown viscous oil that is a mixture of diastereomers. Unreacted starting material (7) is recovered as 0.12 g of a colorless oil. For 8: R$_f$ (CHCl$_3$/MeOH/AcOH 15:3:1) 0.64; $^1$H NMR (CDCl$_3$) 8.03 (d,J=8.1 Hz, 1 H, Ar-3-$\underline{H}$), 7.65 (m, 2 H, Ar-4,5-$\underline{H}$), 7.5 (m, 1 H, Ar-6-$\underline{H}$), 6.8 (two 2, 1 H, 4.61 (two m, 1 H, NC$\underline{H}$), 3.25 (dd,J=17.0, 5.5 Hz, 1 H, C$\underline{H}_2$), 2.92 (br s, 3 H, N Me), 2.09 (s, 1 H, C$\underline{H}_2$), 1.4 (two s, 18 H, C(C$\underline{H}_3$)).

To a pale brown solution of 8 (0.13 g, 0.27 mmol) in dichloromethane (2.0 mL, anhydrous) under argon at room temperature is added TFA (1.0 mL, 13 mmol). The resulting solution is incubated at room temperature for 16 hours, then concentrated in vacuo. Toluene (3 mL) was added to the residue, then re-evaporated in vacuo, leaving an immobile pale brown oil. This oil was purified by chromatography on SEPHADEX LH-20 resin, with water as eluant. After pooling the product fractions, lyophilization yields 90 mg (75%) of 9 as a fluffy colorless powder that is a mixture of diastereomers: m.p. 116°–119° C. (dec.); $^1$H NMR (D$_2$O): 8.15 (d, J=7.9 Hz, 1 H, Ar-3-$\underline{H}$), 7.82 (t,J=7.3 Hz, 1 H, Ar-4-$\underline{H}$), 7.7 (m, 2 H, Ar-5,6-$\underline{H}$), 6.73 (two s, 1 H, ArC$\underline{H}$), 4.23 (br s, 1 H, NC$\underline{H}$), 3.3 (m, 2 H, C$\underline{H}_2$) 2.84 (br s, 3 H, N$\underline{Me}$). Anal. calcd for C$_{15}$H$_{15}$N$_2$O$_{10}$F$_3$: C, 40.92; H, 3.43; N, 6.36. Found: C, 41.24; H, 3.74; N, 6.76.

Example 5. γ-(O-(α-carboxy)-2-nitrobenzyl))-kainic acid hydrochloride salt (12):

(-)-Kainic acid (RBI, 0.25 g, 1.2 mmol) is suspended in a solution of dioxane/water (1:1, 8 mL). Sodium bicarbonate (0.21 g, 2.5 mmol) is added. To the resulting solution is added a solution of t-butylpyrocarbonate (0.44 g, 2.0 mmol) in 1 mL dioxane. The resulting mixture is stirred at room temperature for 16 h, then diluted with water (5 mL). The resulting solution is extracted with EtOAc (3×5 mL) to removed excess pyrocarbonate. The pH of the aqueous portion is adjusted to 2.7 by dropwise addition of 5% HCl, followed by extraction with EtOAc (3×5 mL). The extract is dried (sodium sulfate) and concentrated to give 0.37 g (100%) of N-t-BOC kainic acid as a colorless solid foam: R$_f$(MeCN:H$_2$O:AcOH, 8:1:1) 0.72; $^1$H NMR (CDCl$_3$) 4.96 (br s, 1 H, C═C$\underline{H}_2$), 4.72 (br s, 1 H, C═C$\underline{H}_2$), 3.71 (s, 1 H, NC$\underline{H}$CO$_2$), 3.5 (M, 2 H, NC$\underline{H}_2$), 3.0 (m, 2 H, C$\underline{H}_2$CO$_2$), 2.35 (m, 2 H, CO$_2$CH$_2$C$\underline{H}$), 1.73 (two s, 3 H, C$\underline{H}_3$), 1.43 (two s, 9 H, C(C$\underline{H}_3$)$_3$).

To a colorless solution of N-t-BOC kainic acid (0.18 g, 0.57 mmol) and 1 (0.36 g, 1.14 mmol) in benzene (12 mL) is added diazabicyclo(5.4.0)undec-7-ene (DBU, 0.19 mL, 1.3 mmol). The resulting blue solution is heated at 70° C. for three hours, then cooled and partitioned between EtOAc (10 mL) and water (10 mL). The organic portion is dried over sodium sulfate and concentrated to give a brown gum, which is purified by flash chromatography to give 0.26 g (58%) of 10 as a clear, very pale brown immobile oil, that is a mixture of diastereomers: R$_f$ (5% EtOAc/CHCl$_3$) 0.47; $^1$H NMR (CDCl$_3$) 8.00 (m, 2 H, Ar-3-$\underline{H}$), 7.7 (m, 4 H, Ar-4,5-$\underline{H}$), 7.5 (m, 2 H, Ar-6-$\underline{H}$), 6.8 (m, 2 H, ArC$\underline{H}$), 5.0,4.9 (two br s, 1 H, C═C$\underline{H}_2$), 4.72 (two br s, 1 H, C═C$\underline{H}_2$), 4.4 (two m, 1 H), NC$\underline{H}$CO$_2$), 3.7 (m, 1 H, NC$\underline{H}_2$), 3.5 (m, 1 H NC$\underline{H}_2$), 3.1 (m, 2 H, CO$_2$C$\underline{H}_2$), 2.5 (m, 2 H, CO$_2$CH$_2$C$\underline{H}$, NCH$_2$C$\underline{H}$), 1.8 (four s, 3 H, C$\underline{H}_3$), 1.35 (m, 27 H, C(C$\underline{H}_3$)$_3$).

To a solution of 10 (0.25 g, 0.32 mmol) in dichloromethane (4.0 mL, anhydrous) under argon is added trifluoroacetic acid (TFA, 2.0 mL, 26 mmol). The resulting solution is incubated at room temperature overnight, and evaporated to dryness under vacuum. Toluene (1×5 mL) is added to the residue, and re-evaporated under vacuum. The crude product is then purified by chromatography on SEPHADEX LH-20 resin, using water as eluant. The product fractions are pooled and lyophilized, giving 70 mg (32%) of 11 as a colorless powder that is a mixture of diastereomers: R$_f$(MeCN/H$_2$O/AcOH 8:1:1) 0.55; $^1$H NMR (D$_2$O) 8.1 (m, 2 H, Ar-3-$\underline{H}$), 7.9-7.5 (m, 6 H, Ar-4,5,6-$\underline{H}$), 6.6 (m, 2 H, ArC$\underline{H}$), 5.1,4.9 (m, 2 H, C═C$\underline{H}_2$), 4.2 (dd, J=24, 3.3 Hz, 1 H, NC$\underline{H}$CO$_2$), 3.7-3.4 (m, 2 H, NC$\underline{H}_2$), 3.2-3.0 (m, 2 H, CO$_2$C$\underline{H}_2$), 2.7 (m, 2 H, CO$_2$CH$_2$C$\underline{H}$, NCH$_2$C$\underline{H}$), 1.7 (four s, 3 H, C$\underline{H}_3$). Anal. calcd for C$_{28}$H$_{26}$N$_3$O$_{14}$F$_3$: C, 49.07; H, 3.82; N, 6.13. Found: C, 50.47; H, 4.22; N, 6.18.

The pH of a suspension of 11 (26 mg, 0.038 mmol) in water (2 mL) is raised to 8.5 by careful addition of aqueous NaOH with stirring. The resulting colorless solution is incubated at room temperature for 12 hours, after which the pH is dropped to 1.7 by dropwise addition of aqueous HCl. The resulting solution is applied directly to a column of SEPHADEX LH-20 resin (2×10 cm) which is eluted with water. After the product fractions are pooled and lyophilized, 10 mg (63%) of 12 is collected as a white powder that is a mixture of diastereomers: R$_f$ (MeOH:CHCl$_3$:H$_2$O:AcOH 12.5/10/3.5/0.2) 0.65; $^1$H NMR (D$_2$O) 8.02 (dd,J=8.1, 2.7 Hz, 1 H, Ar-3-$\underline{H}$), 7.71 (t,J=8.0 Hz, 1 H, Ar-5-$\underline{H}$), 7.60 (m, 2 H, Ar-4,6-$\underline{H}$), 6.52 (s, 1 H, ArC$\underline{H}$), 5.0 (C═CH$_2$, integration obscured by solvent peak), 4.13 (dd, J=16.8, 3.3 Hz, 1 H NC$\underline{H}$CO$_2$), 3.54 (m, 1 H, NC$\underline{H}_2$), 3.35 (m, 1 H, NC $\underline{H}_2$), 2.93 (m, 1 H, NCH$_2$C$\underline{H}$), 2.6 (m, 3 H, CO2C$\underline{H}_2$C$\underline{H}$), 1.63, 1.49 (two s, 3 H, C$\underline{H}_3$).

Example 6. α-carboxy-2-nitrobenzyl-caged carbamic acid (17):

A solution of 5,6-carboxy-Q-rhodamine (hydrochloride salt, 13) (120 mg, 0.24 mmol) in DMF (anhydrous, 5 mL) is cooled in an ice bath and treated with a mixture of potassium t-butoxide (88 mg, 0.78 mmol) in dry THF (4 mL) with stirring. More solid potassium t-butoxide is added in 30 mg portions until a cyan color persists. A solution of methyl 2-nitromandelate chloroformate (14) (0.22 g, 0.63 mmol) in dry THF (2 mL) is added, and the resulting pinkish red mixture is stirred at room temperature in darkness overnight. The reaction mixture is acidified with 5% HCl (1 mL) and concentrated in vacuo, and the resulting residue is purified by flash chromatography (15 g silica gel, 40–63μ, 2 cm column) using dichloromethane/EtOAc/AcOH (9:1:0 → 88:10:2) gave the pure caged product (15) as 57 mg of a pale red oil. On a thin layer chromatographic plate, the product is initially non-fluorescent and colorless, becoming pale red and fluorescent orange upon illumination with a handlamp.

The carboxylic acid described above (15) (60 mg, 0.065 mmol) is dissolved in i-PrOH/chloroform (1:1, 8 mL) and treated with diisopropylcarbodiimide (0.16 mmol, 25 μL) and N-hydroxysuccinimide (16 mg, 0.14 mmol). The resulting pale yellow solution is stirred at room temperature in darkness overnight; thin layer chromatography (TLC) showed no remaining starting carboxylic acid. After concentration in vacuo, the resulting pale orange solid is purified by flash chromatography on silica gel (2 cm column, 12 g, 40–63 μM) using 1% i-PrOH/chloroform as eluant. The resulting N-hydroxysuccinimidyl (NHS) ester (16) is obtained as 50 mg of a clear, pale orange immobile oil.

The caging group carboxylates are released by treating the NHS ester (16) (10 mg, 0.01 mmol) with lithium iodide (13 mg, 0.10 mmol) in acetonitrile (2 mL) at 60° C. for 48 hours. The reaction mixture is partitioned between water (2 mL) and EtOAc (2 mL). The organic layer is concentrated, and the residue purified by flash chromatography on silica gel in a pasteur pipette column, using 10% methanol/chloroform as eluant. The product, 17 (carboxy-Q-rhodamine NHS ester, bis-CNBOC-caged where CNBOC=α-carboxy-2-nitrobenzyloxycarbonyl), is obtained as a clear amber immobile oil, that is colorless and non-fluorescent on a thin layer chromatography plate, then pale red and orange fluorescent upon handlamp illumination: R$_f$ (chloroform/methanol/acetic acid, 50:5:1) 0.52; $^1$H NMR (CDCl$_3$) 8.0-7.4 (m, 13 H, aromatic protons), 6.8 (m, 2 H, 4',5' aromatic protons) 6.3 (br s, 2 H, caging group benzylic protons), 3.5 (m, 4 H, NC$\underline{H}_2$), 2.8 (two s, 4 H, NHS methylenes), 2.5 (m, 4 H, NCH$_2$C$\underline{H}_2$CH$_2$), 1.8 (m, 4 H,NCH$_2$CH$_2$C$\underline{H}_2$).

Example 7. α-carboxy-2-nitrobenzyl-caged carbonic acid (Synthesis of α-CNB-carbonate caged uridine.(21)):

t-Butyl-2-nitromandelate: To a suspension of 2-nitromandelic acid (0.86 g, 4.4 mmol) in chloroform (10 mL) with stirring is added O-t-butyl-N,N'-diisopropylisourea (2.7 g, 13 mmol). The resulting mixture is stirred overnight, then filtered. The filtrate is concentrated in vacuo, and the residue purified by flash chromatography using EtOAc/chloroform (0%→5%→10%), giving t-butyl 2-nitromandelate (18) as 0.99 g (90%) of a pale brown clear oil.

t-Butyl 2-nitromandelate chloroformate: To a pale brown solution of t-butyl-2-nitromandelate (0.98 g, 3.9 mmol) and 2,6-lutidine (0.82 mL, 7.0 mmol) in dry THF (5 mL) at room temperature under argon is added phosgene, as a 1.93 M solution in toluene (3.3 mL, 6.4 mmol). The resulting mixture is stirred at room temperature for 5 hours, then filtered using diatomaceous earth. The filtrate is concentrated in vacuo to a pale brown solid, which is flash chromatographed (chloroform) to give a mixture of t-butyl 2-nitromandelate and t-butyl 2-nitromandelate chloroformate (19) as 0.96 g of a pale amber clear oil.

α-CNB-carbonate caged uridine: Uridine (116 mg, 0.5 mmol) is dissolved in anhydrous pyridine (1.5 mL) under argon at room temperature, and chilled in an ice bath. A solution of a mixture of t-butyl-2-nitromandelate and t-butyl-2-nitromandelate chloroformate (19) (0.30 g, estimated to be 50% pure, ca. 0.5 mmol) in 1.0 mL dry THF is added dropwise with stirring. The resulting pale brown mixture is stirred overnight at room temperature. The volatiles are removed in vacuo, and the residue partitioned between EtOAc (15 mL) and saturated sodium bicarbonate (15 mL). The organic layer is washed once with brine, and concentrated in vacuo. Purification of the residue via flash chromatography (MeOH/chloroform 5%→10%) gives three products: $R_f$0.64, 0.46, and 0.28 (CHCl$_3$/MeOH/AcOH 15:3:1); the desired product, 20 (33 mg of a colorless residue), is identified by photolysis experiments, indicating that the middle polarity spot is the only one that photolyzes to free uridine ($R_f$0.09).

Treatment of the O-t-butyl-protected material (20) overnight with trifluoroacetic acid (TFA, 1.0 mL) in dichloromethane (2 mL) overnight at room temperature, followed by evaporation of the volatiles, gives the product α-CNB-carbonate caged uridine (21) as 21 mg of a colorless residue, $R_f$0.19 (CHCl$_3$/MeOH/AcOH 15:3:1). Photolysis experiments, using a handheld UV lamp, show the product photolyzes to free uridine, as determined by co-elution on an analytical thin layer chromatographic plate with an authentic sample.

Example 8. α-carboxy-2-nitrobenzyl-caged carboxylic acid (acetic acid) in which the α-carboxy group is protected as an acetoxymethyl (AM) ester: O-Acetyl-t-butyl-2-nitromandelate: A solution in benzene (2 mL) of t-butyl 2-bromo-2-(o-nitrophenyl)acetate (1) 55 mg, 0.17 mmol), acetic acid (10 µL, 0.17 mmol) and DBU (25 µL, 0.17 mmol) is heated at reflux for 1.5 hours, then diluted with water (3 mL). The aqueous portion is extracted with EtOAc (2×3 mL) and the combined organics concentrated to give a brown oil, which is purified by flash chromatography (chloroform) to give 37 mg of the product (22) as a colorless oil, $R_f$0.19 (chloroform/hexanes 3:1).

Alternatively, the intermediate 22 is prepared by acylation of alcohol 18 with acetic anhydride in organic solvent, catalyzed by the presence of a tertiary amine. O-Acetyl-2-nitromandelic acid. A solution of O-acetyl-t-butyl-2-nitromandelate (22) (33 mg, 0.11 mmol) in 2.5 mL chloroform and TFA (0.35 mL) was incubated at rt for 48 hours, then concentrated. The residue was purified by flash chromatography (MeOH/chloroform, 0→5%) to give the 26 mg of the free carboxylic acid (23) as a clear, pale yellow oil, $R_f$0.33 (CHCl$_3$/MeOH/AcOH 15:3:1).

Acetoxymethyl O-acetyl-2-nitromandelic acid (24): A pale brown solution of O-Acetyl-2-nitromandelic acid (23) (14 mg, 0.059 mmol), bromomethyl acetate (10 µL, 0.10 mmol), and triethylamine (10 µL, 0.072 mmol) in chloroform (1 mL) is incubated overnight. The volatiles are removed in vacuo, and the residue is purified by flash chromatography (chloroform) to give 16 mg of the title compound (24) as a clear colorless oil, $R_f$0.65 (5% MeOH/chloroform.

Example 9. α-Carboxy-2-nitrobenzyl-caged carboxylic acid (acetic acid) via a diazo intermediate:

An equimolar diethyl ether solution of acetic acid and diazoacetate 25 ($R_f$0.60, CHCl$_3$; prepared by diazo transfer from tosyl azide to t-butyl 2-nitrophenylacetic acid, mediated by KF/Al$_2$O$_3$) is stirred at room temperature. A drop of BF$_3$.Et$_2$O is added, discharging the previous yellow color and resulting in vigorous gas evolution. Formation of 22 is evidenced by formation of a colorless quenching spot, $R_f$0.45.

Example 10. γ-O-(α-carboxy-2-nitrobenzyl)-caged ATP (27):

A solution of ATP, disodium salt in E-pure water at pH 3.4 is treated with a yellow diethyl ether solution containing an excess of t-butyl 2-(o-nitrophenyl)dizaoacetate (25) at room temperature. Vigorous stirring of the resulting bi-phasic solution for two days gives the alkylated product, 26, as verified by thin layer chromatographic analysis; starting ATP $R_f$=0.0, and product $R_f$=0.70 (MeOH/CHCl$_3$/H$_2$O/AcOH 12.5:10:3.5:0.2). This constitutes a formal synthesis of γ-O-(α-carboxy-2-nitrobenzyl)-caged ATP (27), as treatment of 26 with TFA selectively cleaves the caging group t-butyl ester to give 27.

Example 11. α-CNB-Caged Nucleoside Triphosphate:

The hydroxyl group oft-butyl 2-nitromandelate (18) is phosphorylated with phosphorous oxychloride; followed by hydrolysis and acidification to give the phosphate ester. Conversion of the phosphate ester to the aniline salt, followed by coupling with "activiated" imidazole adenosine diphosphate using the methodology described in J. AM. CHEM. SOC., 115, 6001 (1993) gives (α-carboxy-2-nitrobenzyl)-caged ATP in which the carboxylate is protected as the t-butyl ester (26). Subsequent treatment with TFA selectively cleaves the t-butyl ester, giving γ-O-(α-carboxy-2-nitrobenzyl)-caged ATP (27).

Example 12. S-(α-carboxy-2-nitrobenzyl)-caged cysteine (29):

Treatment of N-t-BOC cysteine in DMF with one equivalent of 1, mediated by triethylamine, alkylates the thiol to give 28, t-butyl protected caged cysteine. Subsequent treatment with TFA concomitantly cleaves the N-t-BOC group and the t-butyl ester, giving 29.

Example 13. S-(α-carboxy-2-nitrobenzyl):caged nucleotide triphosphate

Reaction of γ-S-GTP with 1 in DMF, mediated by triethylamine, gives the protected s-caged nucleotide, 30. Subsequent TFA treatment cleaves the t-butyl ester to give the S-(α-carboxy-2-nitrobenzyl)-caged nucleotide triphosphate (31).

Example 14. O-(α-carboxy-2-nitrobenzyl)-caged A-23187:

Treatment of the ionophore A-23187 with one equivalent of 1 in refluxing benzene, mediated by DBU, yields the protected intermediate 32. Subsequent treatment with TFA gives the O-(α-carboxy-2-nitrobenzyl)-caged A-23187 (33).

Figure 1:
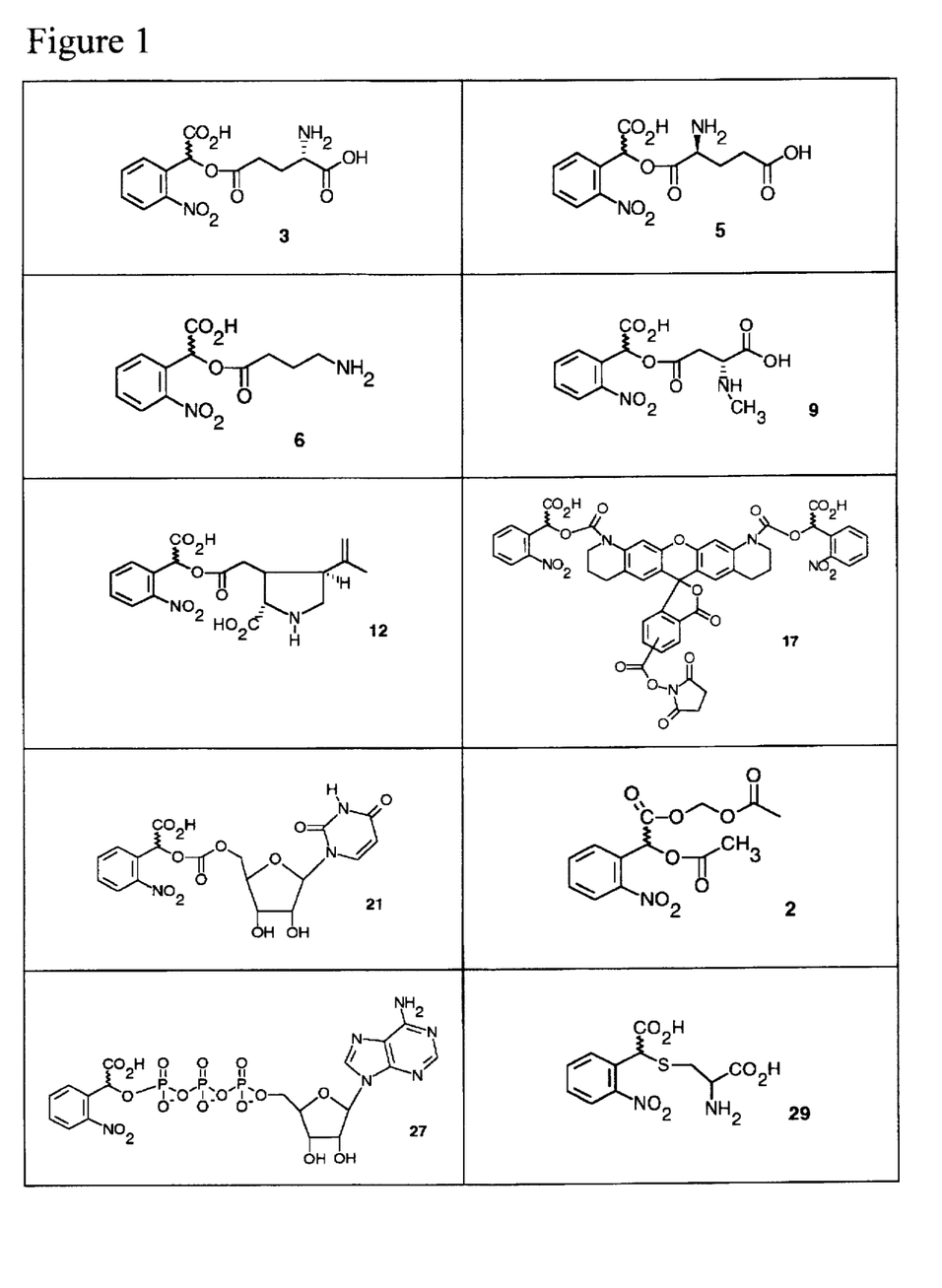
FIG. 1: Selected embodiments of the present invention.
Figure 2:
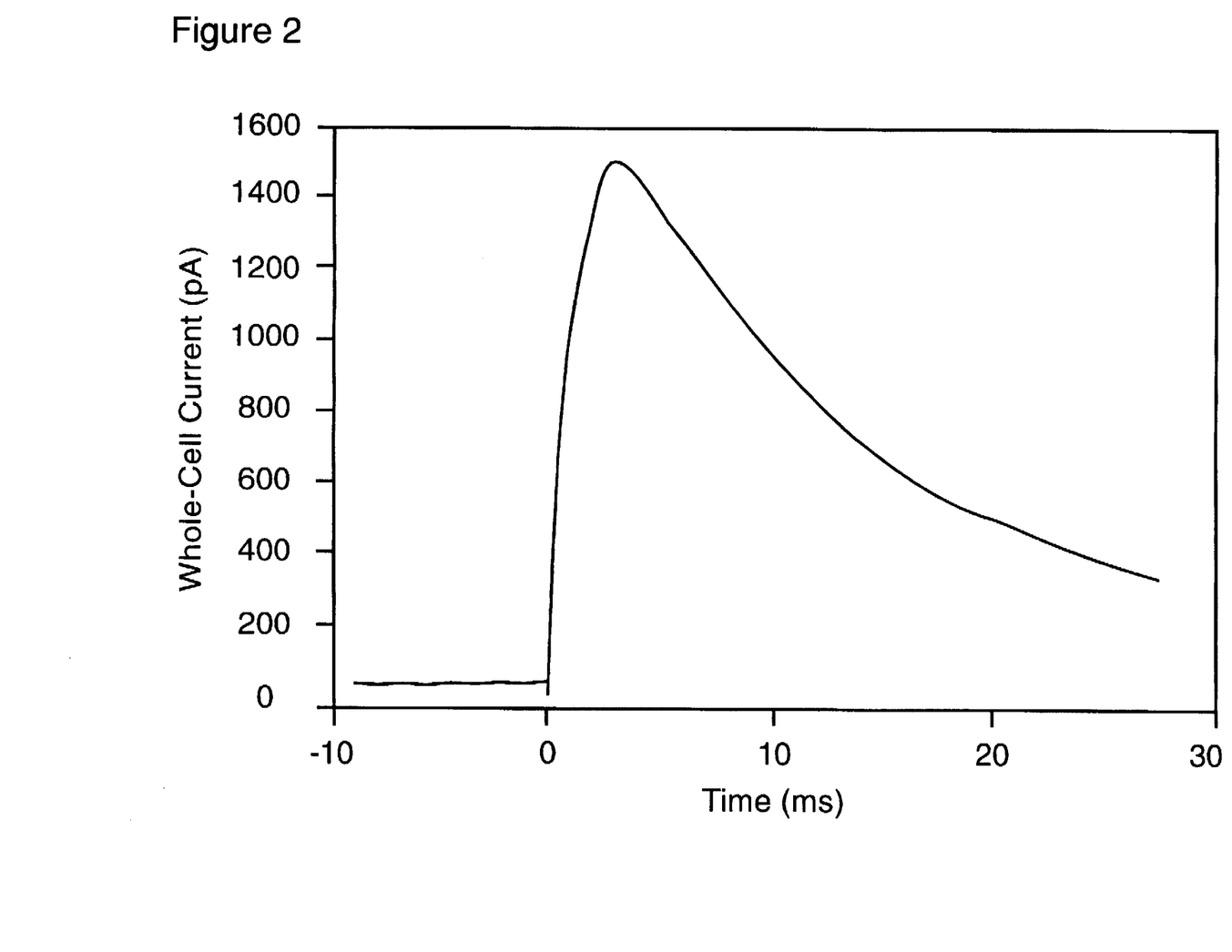

Example 15. Release of a caged neurotransmitter in situ:

A whole neuron is bathed in a solution of γ-(α-carboxy o-nitrobenzyl)-caged glutamic acid (3), as described in Example 1. The whole-cell current is then monitored as the neuron is photolyrically illuminated at 343 nm. As shown in FIG. 2, the whole-cell current increases rapidly at time=0 ms, when illumination is begun. This indicates both that the uncaging of a CNB-caged probe is extremely rapid, but also verifies that the caged neurotransmitter is inert in situ until uncaged.

Figure 3:
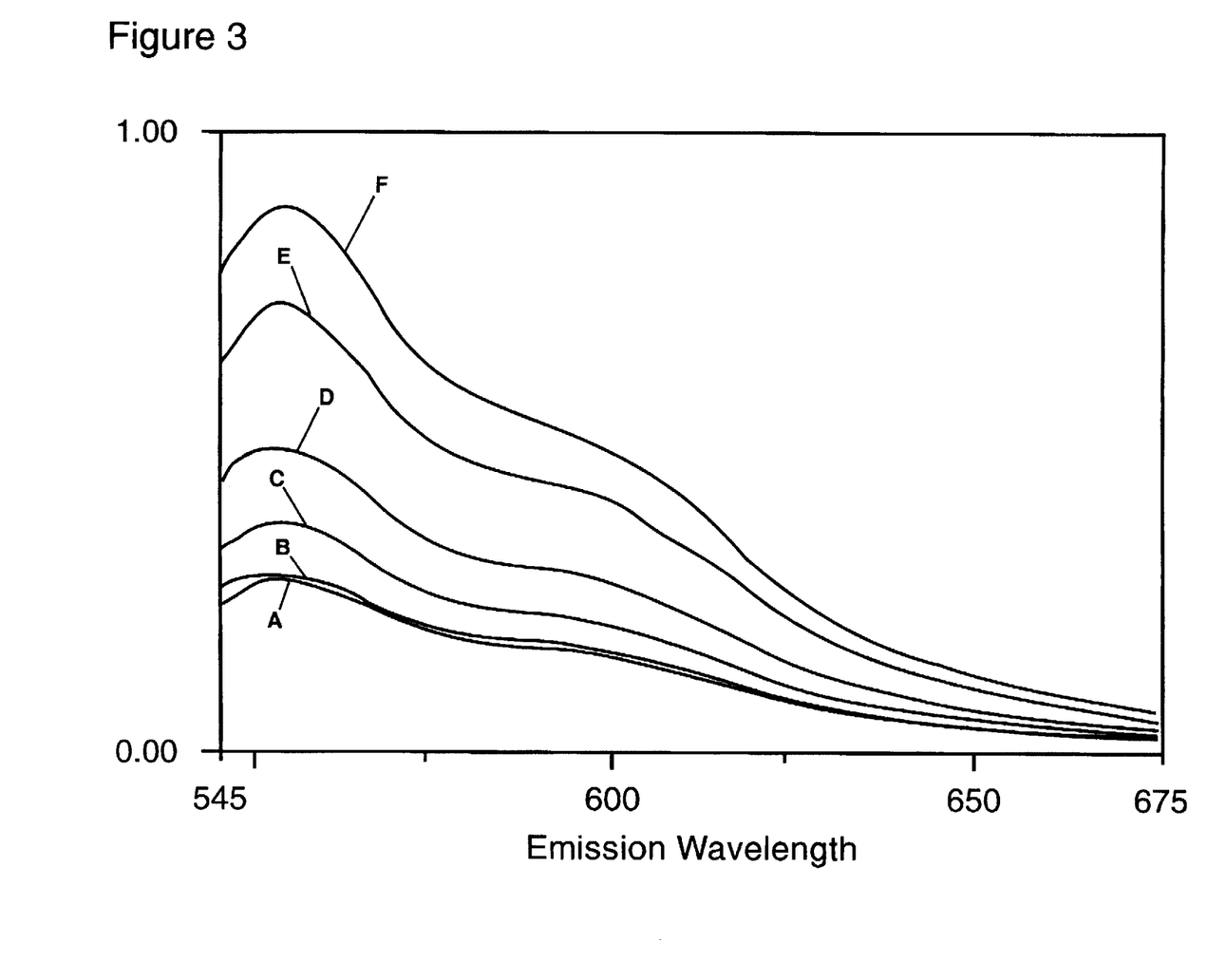
FIG. 3: The photolysis of a caged fluorescent dye (as described in Example 16). The increase in fluorescence emission as a function of time indicates that the caged dye is non-fluorescent, but becomes highly fluorescent upon photolysis.

Example 16. Release of a caged fluorescent dye:

A 0.5 mM solution of 17 (as described in Example 6) in methanol is photolysed at 310 nm in a fluorometer (as shown in FIG. 3). The fluorescence spectrum is recorded as the caged dye is released, using excitation at 538 nm. The fluorescence emission of the sample increases as a function of photolysis time, as free dye is released.

| Spectrum | Time (min) | Emission Intensity |
|---|---|---|
| A | 0 | 0.27 |
| B | 2 | 0.28 |
| C | 10 | 0.32 |
| D | 20 | 0.49 |
| E | 40 | 0.73 |
| F | 60 | 0.88 |

It is to be understood that, while the foregoing invention has been described in detail by way of illustration and example, numerous modifications, substitutions, and alterations are possible without departing from the spirit and scope of the invention as described in the following claims.

What is claimed is:

1. A photolabile compound, having the formula wherein $R^1$ and $R^2$, which may be the same or different, are H, —(C=O)—Cl, $CO_2R^7$, —$OR^8$, —O—$(CH_2)_n$—$CO_2R^7$;

wherein $R^7$ is H, a linear or branched alkyl ester having 1–6 carbons, —$CH_2$—O—(C=O)—$CH_3$, or a carboxylate salt, and $R^8$ is a linear or branched alkyl having 1–18 carbons;

n=1–17;

$R^3$ is H or —$NO_2$;

$R^4$, is H, a linear or branched alkyl ester having 1–6 carbons, —$CH_2$—O—(C=O)—$CH_3$, or a carboxylate salt;

X is and $R^5$ is selected so that photolysis of said photolabile compound generates a linear or branched, saturated or unsaturated, substituted or unsubstituted carboxylic acid that is a fatty acid having 3–32 carbons;

or $R^5$ is selected so that photolysis of said photolabile compound generates a glutamic acid, an aspartic acid, or a γ-aminobutyric acid.

2. A compound, as claimed in claim 1 wherein said carboxylic acid is a prostaglandin.

3. A compound, as claimed in claim 1, wherein said carboxylic acid is arachidonic acid.

4. A compound, as claimed in claim 1, wherein said carboxylic acid is domoic acid.

5. A photolabile compound, having the formula wherein $R^1$ and $R^2$ which may be the same or different, are H, —(C=O)—Cl, $CO_2R^7$, —$OR^8$, —O—$(CH_2)_n$—$CO_2R^7$, or $R^1$ and $R^2$ taken in combination are —O—$CH_2$—O—;

wherein $R^7$ is H, a linear or branched alkyl ester having 1–6 carbons, —$CH_2$—O—(C=O)—$CH_3$, or a carboxylate salt, and $R^8$ is a linear or branched alkyl having 1–18 carbons;

n=1–17;

$R^3$ is H or —$NO_2$;

$R^4$ is H, a linear or branched alkyl ester having 1–6 carbons, —$CH_2$—O—(C=O)—$CH_3$, or a carboxylate salt;

X is wherein $R^5$ and $R^6$ are selected so that photolysis of said photolabile compound generates an amino acid, peptide or protein;

or X is and $R^5$ is selected so that photolysis of said photolabile compound generates a linear or branched, saturated or unsaturated, substituted or unsubstituted carboxylic acid that is a fatty acid having less than 32 carbons.

6. A compound, as claimed in claim 5, wherein said amino acid is caged through a carboxylic acid as an ester.

7. A compound, as claimed in claim 5, wherein said amino acid is caged through a α-nitrogen or a non-α-nitrogen atom as a carbamate.

8. A compound, as claimed in claim 5, wherein said amino acid is caged through a side-chain hydroxyl as an ether or carbonate.

9. A compound, as claimed in claim 5, wherein said amino acid is caged through a side chain thiol as a thioether.

10. A compound, as claimed in claim 5, wherein $R^1$ and $R^2$, which may be the same or different, are H, —(C=O)—Cl, —CO$_2$R$^7$, —OR$^8$, or —O—(CH$_2$)$_n$—CO$_2$R$^7$;

wherein $R^7$ is H, a linear or branched alkyl ester having 1-6 carbons, —CH$_2$—O—(C=O)—CH$_3$, or a carboxylate salt, and $R^8$ is a linear or branched alkyl having 1-18 carbons;

n=1-17;

$R^3$ is H or —NO$_2$;

$R^4$ is H, a linear or branched alkyl ester having 1-6 carbons, —CH$_2$—O—(C=O)—CH$_3$, or a carboxylate salt;

X is —O—(C=O)—R$^5$;

wherein $R^5$ is selected so that photolysis of said photolabile compound generates a serine, threonine, tyrosine, lysine, glutamic acid, or aspartic acid.

11. A compound, as claimed in claim 1, wherein $R^1$, $R^2$, $R^3$ and $R^4$ are hydrogen.

12. A photolabile compound, having the formula wherein $R^1$ and $R^2$, which may be the same or different, are H, —(C=O)—Cl, —CO$_2$R$^7$ —OR$^8$, or —O—(CH$_2$)$_n$—CO$_2$R$^7$, or $R^1$ and $R^2$ taken in combination are —O—CH$_2$—O—;

wherein $R^7$ is H, a linear or branched alkyl ester having 1-6 carbons, —CH$_2$—O—(C=O)—CH$_3$, or a carboxylate salt, and $R^8$ is a linear or branched alkyl having 1-18 carbons;

n=1-17;

$R^3$ is H or —NO$_2$;

$R^4$ is H, a linear or branched alkyl ester having 1-6 carbons, —CH$_2$—O—(C=O)—CH$_3$, or a carboxylate salt;

X is wherein $R^5$ and $R^6$ are selected so that photolysis of said photolabile compound generates a carbohydrate that is a monosaccharide, disaccharide or a polysaccharide.

13. A compound, as claimed in claim 12, wherein said carbohydrate is caged as an ether or carbonate of an aliphatic hydroxyl group.

14. A compound, as claimed in claim 12, wherein said carbohydrate is caged as a carbamate of an amino group.

15. A compound, as claimed in claim 12, wherein said carbohydrate is caged as an ester of a carboxylic acid or of a phosphate or thiophosphate group.

16. A photolabile compound, having the formula wherein

R$^1$ and R$^2$, which may be the same or different, are H, —(C=O)-Cl, —CO$_2$R$^7$, —OR$^8$, or —O—(CH$_2$)$_n$—CO$_2$R$^7$, or R$^1$ and R$^2$ taken in combination are —O—CH$_2$—O—;

wherein R$^7$ is H, a linear or branched alkyl ester having 1–6 carbons, —CH$_2$—O—(C=O)—CH$_3$, or a carboxylate salt, and R$^8$ is a linear or branched alkyl having 1–18 carbons;

n=1–17;

R$^3$ is H or —NO$_2$;

R$^4$ is H, a linear or branched alkyl ester having 1–6 carbons, —CH$_2$—O—(C=O)—CH$_3$, or a carboxylate salt;

X is wherein R$^5$ and R$^6$ are selected so that photolysis of said photolabile compound generates a nucleoside, a nucleotide or an oligonucleotide.

17. A compound, as claimed in claim 16, wherein said nucleoside, nucleotide or oligonucleotide is caged as an ether or carbonate ester of a carbohydrate portion of said nucleoside, nucleotide or oligonucleotide;

or caged as an ether or carbonate ester of a hydroxyl function attached directly or indirectly to a base portion of said nucleoside, nucleotide or oligonucleotide.

18. A compound, as claimed in claim 16, wherein said nucleoside, nucleotide or oligonucleotide is caged as a carbamate derivative at a nitrogen atom of a base portion of said nucleoside, nucleotide or oligonucleotide.

19. A compound, as claimed in claim 16, wherein said nucleotide or oligonucleotide is caged as a phosphate monoester, phosphodiester or thiophosphate at a phosphate portion of said nucleotide or oligonucleotide.

20. A photolabile compound, having the formula wherein

R$^1$ and R$^2$, which may be the same or different, are H, —(C=O)—Cl, —CO$_2$R$^7$, —OR$^8$, or —O—(CH$_2$)$_n$—CO$_2$R$^7$;

wherein R$^7$ is H, a linear or branched alkyl ester having 1–6 carbons, —CH$_2$—O—(C=O)—CH$_3$, or a carboxylate salt, and R$^8$ is a linear or branched alkyl having 1–18 carbons;

n=1–17;

R$^3$ is H or —NO$_2$;

R$^4$ is H, a linear or branched alkyl ester having 1–6 carbons, —CH$_2$—O—(C=O)—CH$_3$, or a carboxylate salt;

X is —O—(C=O)—R$^5$;

wherein $R^5$ is selected so that photolysis of said photolabile compound generates a glutamic acid, an arachidonic acid, a γ-aminobutyric acid, a N-methyl-D-aspartic acid, a kainate, a 1-aminocyclopentane-1,3-dicarboxylate, a quisqualate, or a glucuronic acid.

21. A compound, as claimed in claim 20, wherein $R^1$, $R^2$ and $R^3$ are hydrogen.

22. A compound, as claimed in claim 20 wherein photolysis of said photolabile compound generates a glutamic acid, a γ-aminobutyric acid, a N-methyl-D-aspartic acid, a kainate, a 1-aminocyclopentane-1,3-dicarboxylate, or a quisqualate.

23. A photolabile compound, having the formula wherein $R^1$ and $R^2$ which may be the same or different, are H, —(C=O)—Cl, —CO$_1$R$^7$, —OR$^8$, or —O—(CH$_2$)$_n$—CO$_2$R$^7$, or $R^1$ and $R^2$ taken in combination are —O—CH$_2$—O—;

wherein $R^7$ is H, a linear or branched alkyl ester having 1–6 carbons, —CH$_2$—O—(C=O)—CH$_3$, or a carboxylate salt, and $R^8$ is a linear or branched alkyl having 1–18 carbons;

n=1–17;

$R^3$ is H or —NO$_2$;

$R^4$ is H, a linear or branched alkyl ester having 1–6 carbons, —CH$_2$—O—(C=O)—CH$_3$, or a carboxylate salt;

and X is

* * * * *

UNITED STATES PATENT AND TRADEMARK OFFICE
CERTIFICATE OF CORRECTION

PATENT NO. : 5,635,608
DATED : June 3, 1997
INVENTOR(S) : Haugland, et al.

It is certified that error appears in the above-indentified patent and that said Letters Patent is hereby corrected as shown below:

At col 1, line 59, "Mother" should be --Another--.

At col 1, line 61, "dishes" should be --diminishes--.

At col 6, line 48, "beating" should be --bearing--.

At col 10, line 43, "Ha" should be --Hz--.

At col 14, line 16, "$BF_3.Et_2O$" should be --$BF_3 \cdot Et_2O$--.

At Claim 23, col 22, lines 27-30 should appear as follows:

Signed and Sealed this

Ninth Day of September, 1997

Attest:

BRUCE LEHMAN

Attesting Officer

Commissioner of Patents and Trademarks